United States Patent [19]
Watanabe et al.

[11] Patent Number: 5,734,059
[45] Date of Patent: Mar. 31, 1998

[54] PRODUCTION INTERMEDIATE AND PROCESS FOR PRODUCING PYRIDINE DERIVATIVE

[75] Inventors: Syotaro Watanabe, Saitama, Japan; William R. Kem; Hun Ju Lee, both of Gainsville, Fla.; Makoto Kajitani; Kazuo Maruhashi, both of Saitama, Japan

[73] Assignees: Taiho Pharmaceutical Co., Ltd., Toyko, Japan; University of Florida, Gainsville, Fla.

[21] Appl. No.: 809,467
[22] PCT Filed: Sep. 21, 1995
[86] PCT No.: PCT/JP95/01911
   § 371 Date: Mar. 20, 1997
   § 102(e) Date: Mar. 20, 1997
[87] PCT Pub. No.: WO96/09300
   PCT Pub. Date: Mar. 28, 1996

[30] Foreign Application Priority Data

Sep. 22, 1994 [JP] Japan ................. 6-252726

[51] Int. Cl.⁶ ................................. C07D 401/04
[52] U.S. Cl. ................................. 546/193
[58] Field of Search ................................. 546/193

[56] References Cited

FOREIGN PATENT DOCUMENTS

WO 92/15306  9/1992  WIPO.

OTHER PUBLICATIONS

Ber., 61, 327 (1928).
Chem. Ber., 69, 1082–1085 (1936).
Chemical Abstract of JP-B-39-25048 (1965).
Acta Chem. Scand., 30B, 93 (1976).
Synth. commun., 2(4), 187–200 (1972).
Tetrahedoron lett., 24, (18), 1937–1940 (1983).
J. Org. Chem., 54(1), 228–234 (1989).

*Primary Examiner*—Patricia L. Morris
*Attorney, Agent, or Firm*—Sughrue, Mion, Zinn, Macpeak & Seas, PLLC

[57] ABSTRACT

This invention relates to: (1) a compound represented by the formula (V), its tautomer and a mixture of the same; (2) a process for producing the compound represented by the above-mentioned formula (V), its tautomer or a mixture of the same, which comprises reacting N-vinylpiperidone represented by the formula (I) with a nicotinate represented by the formula (II), wherein R represents a lower alkyl group, in the presence of a sodium alkoxide; (3) a process for producing a pyridine derivative represented by the formula (III), which comprises producing the compound represented by the formula (V), its tautomer or a mixture of the same by the process as described in the above (2), and then treating the obtained compound with an acid; and (4) a process for producing a pyridine derivative represented by the formula (IV), in which the treatment with an acid as described in the above (3) is followed by another treatment with a base. Thus, the present invention provides industrial processes for producing pyridine derivatives represented by the formulae (III) and (IV) safely, economically, easily and efficiently without using any hazardous reagents.

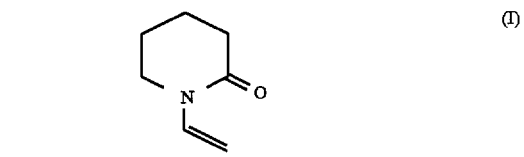

(I)

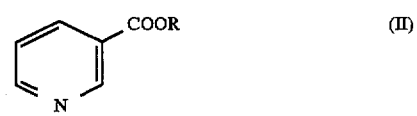

(II)

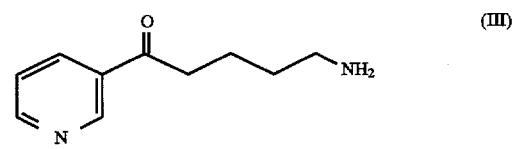

(III)

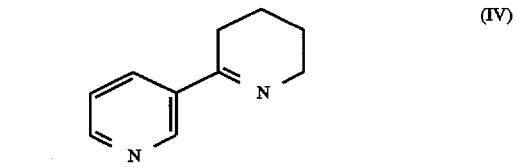

(IV)

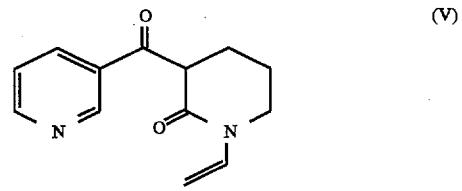

(V)

4 Claims, No Drawings

PRODUCTION INTERMEDIATE AND PROCESS FOR PRODUCING PYRIDINE DERIVATIVE

This is a 371 of PCT/JP95/01911 filed Sep. 21, 1995.

TECHNICAL FIELD

This invention relates to novel production intermediates to be used for the production of pyridine derivatives (e.g., anabaseine), which are useful for the treatment of central nervous system diseases such as Alzheimer's disease and Parkinson's disease, and industrial processes for producing the same.

BACKGROUND ART

A pyridine derivative represented by formula (III):

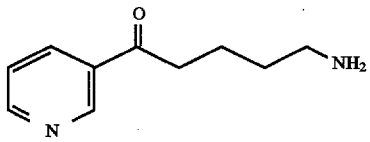

anabaseine represented by formula (IV):

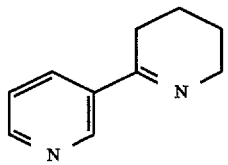

and anabaseine derivatives obtained by using the above-mentioned compound (III) or (IV) as a synthesis intermediate are publicly known compounds described in, for example, Brit. J. Pharmacol., 18, 543 (1962), Agr. Biol. Chem, 26, 709 (1962), Toxicon, 9, 23 (1971), Amer. Zoologist, 25, 99 (1985), Drug Development Research, 31, 127 (1994) or 31, 135 (1994), International Publication Nos. WO 92/15306 and WO 94/05288. These compounds are useful as a remedy for central nervous system diseases such as Alzheimer's disease and Parkinson's disease.

As processes for producing the pyridine derivatives represented by the formula (III) and their analogous compounds, there have been publicly known some methods with the use of a sodium alkoxides as a base, for example, (1) a method for producing nicotine by reacting a nicotinate with N-methylpyrrolidone with the use of sodium ethoxide (Ber., 61., 327 (1928)); and (2) another method for producing anabaseine from N-benzoylpiperidone and ethyl nicotinate with the use of sodium ethoxide (Chem. Ber., 69, 1082–1085 (1936)). However, these methods can achieve only low yields, i.e., 37.5% and 20.5% respectively. In the method [2], furthermore, the reaction is accompanied by a rapid increase in temperature, which makes it difficult to control the reaction temperature. In this case, moreover, 2-phenyl-3,4,5,6-tetrahydropyridine is formed as a side-product which can be hardly eliminated on an industrial scale. Accordingly, these existing methods are not preferable form an industrial viewpoint.

Subsequently, there have been proposed some methods wherein the sodium alkoxide is replaced by sodium hydride with an elevated basicity to thereby accelerate the progress of the reaction. Examples of these methods include (3) a method for producing nicotinoyl-N-methylpyrrolidone from a nicotinate and N-methylpyrrolidone with the use of sodium hydride (JP-B-39-25048; the term "JP-B" as used herein means an "examined Japanese patent publication"); and (4) a method for producing myosmin from N-vinylpyrrolidone and a nicotinate with the use of sodium hydride (Acta Chem. Scand., 30B, 93 (1976)). Although these methods contribute to the improvement in yield, the industrial application thereof is accompanied by serious problems. That is to say, the sodium hydride employed as a reagent in these methods spontaneously ignites when it comes in contact with air. Also, it catches fire easily in the presence of water. At the reaction, it undergoes vigorous foaming and causes heat generation and evolution of hydrogen gas. Due to these characteristics, it is highly dangerous to use sodium hydride in the synthesis on a large scale. To ensure the security, therefore, specific devices and techniques are required. Moreover, sodium hydride is usually marketed in a state of being dispersed in liquid paraffin in an amount of about 60%. Accordingly, the production process should involve an additional step of completely eliminating the liquid paraffin. Thus, it is to be concluded that the above-mentioned methods with the use of sodium hydride are unsuitable for industrial purposes from an economical viewpoint too.

Examples of other production methods include (5) a method starting from N-nicotinoylpiperidone with the use of calcium oxide (Synth. Commun., 2 (4), 187–200 (1972)); (6) a method starting from bromopyridine and cyclopentanone with the use of n-butyllithium (Tetrahedron Lett., 24 (18), 1937–1940 (1983)); (7) a method wherein bromopyridine is condensed with N-tert-butyloxycarbonylpiperidone with the use of n-butyllithium (J. Org. Chem., 54 (1), 228–234 (1989)); and (8) a method wherein N-trimethylsilylpiperidone is condensed with a nicotinate derivative with the use of lithium diisorpopylamide (International Publication WO 92/15306). However, it has been clarified that these methods also suffer from various problems. Namely, the method (5), wherein the starting material is molten by heating over an open fire in the presence of calcium oxide, is highly dangerous and thus unsuitable as an industrial process. In the methods (6), (7) and (8), on the other hand, the reactions should be performed at a low temperature (−70° C. or below) with the use of n-butyllithium or lithium diisopropylamide. Thus, these methods are not preferable as industrial processes from the viewpoints of economics and safety.

Therefore, it has been urgently required to develop an industrial process by which the pyridine derivatives represented by the formulae (III) and (IV) can be produced safely economically, easily and efficiently without using any hazardous reagent.

DISCLOSURE OF THE INVENTION

The present inventors have conducted extensive studies to establish an industrial process which is excellent in safety, economics, convenience and efficiency. As a result, they have unexpectedly found out a novel synthesis intermediate, which is useful for the production of the compounds (III) and (IV), and a production process with the use of the same by using a sodium alkoxide with piperidone protected with a specific N-protecting group, thus completing the present invention. Accordingly, the present invention relates to:

(1) a compound represented by formula (V):

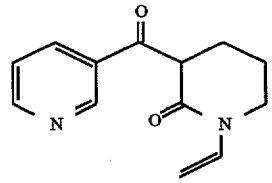

its tautomer and a mixture of the same;

(2) a process for producing the compound represented by the formula (V), its tautomer or a mixture of the same as described in the above (1), which comprises reacting N-vinylpiperidone represented by formula (I):

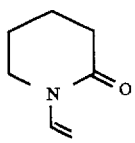   (I)

with a nicotinate represented by formula (II):

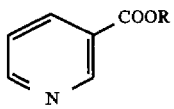   (II)

wherein R represents a lower alkyl group; in the presence of a sodium alkoxide;

(3) a process for producing the compound represented by the formula (V), its tautomer or a mixture of the same as described in the above (2), wherein said sodium alkoxide is sodium ethoxide;

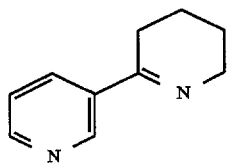   (IV)

wherein the treatment with an acid as described in the above (5) is followed by another treatment with a base.

Now, the present invention will be illustrated by reference to the following reaction scheme.

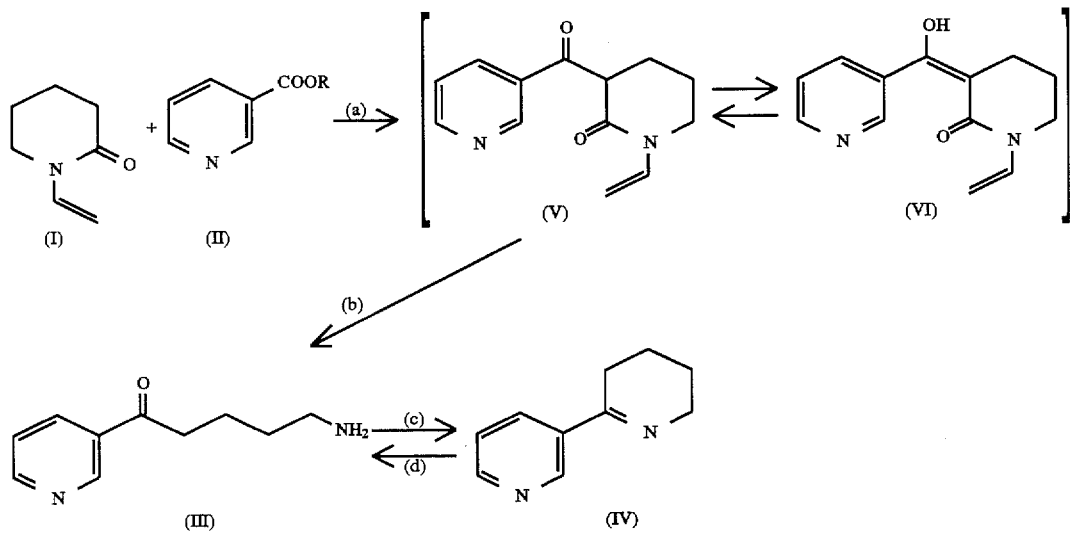

(4) a process for producing the compound represented by the formula (V), its tautomer or a mixture of the same as described in the above (2), wherein R in the formula (II) is an ethyl group and the sodium alkoxide is sodium ethoxide;

(5) a process for producing a pyridine derivative represented by formula (III):

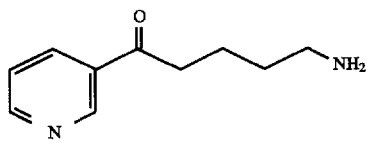   (III)

which comprises producing the compound represented by the formula (V), its tautomer or a mixture of the same by the process as described in any of the above (2), (3) and (4), and then treating the obtained compound with an acid; and (6) a process for producing a pyridine derivative represented by formula (IV):

In the step (a) of the above reaction scheme, publicly known compounds (I) and (II) are reacted in an appropriate solvent in the presence of a sodium alkoxide to thereby give a compound represented by the formula (V) or (VI). The compound represented by the formula (V) is 3-nicotinoyl-1-vinyl-2-piperidinone, while the compound represented by the formula (VI) is the tautomer of the same.

The lower alkyl group represented by R in the compound (II) is a linear or branched alkyl group having 1 to 4 carbon atoms. Typical examples thereof include methyl, ethyl, propyl, isopropyl, n-butyl, sec-butyl and tert-butyl groups. It is preferable that R represents a methyl or ethyl group, still preferably an ethyl group.

Examples of the sodium alkoxide usable in this step include sodium methoxide, sodium ethoxide, sodium propoxide and sodium tert-butoxide. It is preferable to use sodium methoxide or sodium ethoxide, still preferably sodium ethoxide, therefor.

The solvent to be used in this step is not particularly limited, so long as it exerts no undesirable effect on the reaction. Examples thereof include hydrocarbons such as benzene, toluene and xylene, ethers such as dimethoxyethane, tetrahydrofuran and dioxane, alcohols such as methanol, ethanol and propanol and aprotic polar solvents such as N,N-dimethylformamide. Among them, it is preferable to use toluene, xylene, tetrahydrofuran or dimethoxyethane therefor. Neither the reaction temperature nor the reaction time is particularly restricted. In general, the reaction is performed at −5° to 150° C., preferably from room temperature to the reflux temperature of the solvent, for 1 to 20 hours, preferably 2 to 6 hours. The reaction can be advantageously carried out by using from 0.5 to 2 mol (preferably from 0.8 to 1.2 mol) of the compound of the formula (II) and from 1 to 4 mol (preferably from 1.5 to 3.0 mol) of the sodium alkoxide each per mol of the compound represented by the formula (I).

The compounds represented by the formulae (V) and (VI), which have been optionally isolated from each other, are then employed in the step (b). Although the solvent is usually eliminated from these compounds prior to the use in the step (b), these compounds may be employed in the step (b) as such.

In the step (b) of the above reaction scheme, the compound represented by the formula (v) or (VI) obtained in the step (a) is treated by adding an acid in an appropriate aqueous solvent to thereby give a compound represented by the formula (III) via devinylation, hydrolysis and decarboxylation. The solvent to be used in this step is not particularly limited, so long as it exerts no undesirable effect on the reaction. Examples thereof include hydrocarbons such as benzene, toluene and xylene, ethers such as dimethoxyethane, tetrahydrofuran (THF) and dioxane, alcohol is such as methanol, ethanol, propanol and isopropanol and water. Among all, it is preferable to use methanol, ethanol, isopropanol or water therefor.

Examples of the acid to be used in the step (b) include inorganic acids such as hydrochloric acid, hydrobromic acid, sulfuric acid and nitric acid and organic acids such as acetic acid, p-toluenesulfonic acid, benzenesulfonic acid, methanesulfonic acid and trifluoroacetic acid. It is preferable to use hydrochloric acid, hydrobromic acid or sulfuric acid therefor. Neither the reaction temperature nor the reaction time is particularly restricted. In general, the reaction is performed at 50° to 150° C., preferably from room temperature to the reflux temperature of the solvent, for 1 to 10 hours, preferably 1 to 5 hours.

The compound represented by the formula (III) obtained in this step can be isolated in the form of a salt of the acid employed. The compound (III), which has been optionally isolated, is then employed in the step (c).

In the step (c), the compound (III) obtained in the step (b) is treated with a base in an appropriate aqueous solvent to thereby give a compound (IV).

The base to be used in this step is not particularly limited, so long as it exerts no undesirable effect on the reaction. Examples thereof generally include alkali metal hydroxides such as sodium hydroxide and potassium hydroxide, alkali metal carbonates such as sodium carbonate and potassium carbonate, alkali metal phosphates such as sodium phosphate and potassium phosphate, inorganic bases such as aqueous ammonia and anionic ion exchange resins. It is preferable to use sodium hydroxide or potassium hydroxide therefor. As the solvent, use can be made of those cited in the step (b) too. The reaction is performed at 0° to 50° C., preferably at room temperature, though the reaction temperature is not particularly restricted. By regulating the pH value to 9 to 12, the compound (IV) can be obtained.

For the purpose of reference, it is indicated that the compound (IV) obtained in the step (c) can be given in the form of a salt of an acid with the use of the compound (III) by treating with the acid in an appropriate aqueous solvent as shown by the step (d). As the solvent and acid to be used in this step (d), use can be made of those cited in the step (b).

Neither the reaction temperature nor the reaction time is particularly restricted. In general, the reaction is performed at 0° to 100° C., preferably 0° to 50° C., for 1 to 17 hours, preferably 1 to 4 hours.

The compound obtained by the present invention can be isolated and purified by conventionally known means for separation and purification such as distillation, recrystallization, silica gel chromatography, etc.

BEST MODE FOR CARRYING OUT THE INVENTION

To further illustrate the present invention in greater detail, the following Examples and Reference Example will be given.

Example 1: Synthesis of 3-nicotinoyl-1-vinyl-2-piperidinone (compound of the formula (V))

25.5 g (375 mmol) of sodium ethoxide was added to 250 ml of tetrahydrofuran (THF). While heating under reflux, a solution of 31.25 g (250 mmol) of N-vinylpiperidone and 37.75 g (250 mmol) of ethyl nicotinate in tetrahydrofuran (75 ml) was added thereto and the resulting mixture was refluxed for 3 hours. Then, it was cooled to 10° C. or below and 175 ml of a saturated aqueous solution of ammonium chloride was added. The organic layer was separated and the aqueous layer was further extracted with 200 ml portions of ethyl acetate twice. The extracts were combined with the above-mentioned organic layer and dried with sodium sulfate. After filtering off the sodium sulfate, the filtrate was concentrated under reduced pressure and dried. Thus, 52.71 g of a mixture of the keto-enol tautomers of the title compound was obtained (yield: 91.6%). This mixture was added to 150 ml of diisopropyl ether and stirred at room temperature for 1 hour. After filtering and drying under reduced pressure, 32.9 g of the title compound (keto-form) was obtained (yield: 57.1%). IR spectrum (KBr) $v_{max}$: 1627 $cm^{-1}$.

NMR spectrum ($CDCl_3$, internal standard: tetramethylsilane, δ ppm):

1.7–2.4 (4H, m); 3.4–3.6 (2H, m); 4.4–4.6 (3H, m); 7.4–7.6 (2H, m); 8.3–9.3 (3H, m).

Example 2: Synthesis of 3-(5-amino-1-pentanoyl) pyridine dihydrochloride (dihydrochloride of compound of the formula (III))

4.6 g (keto-form, 20 mol) of the 3-nicotinoyl-1-vinyl-2-piperidinone obtained in Example 1 was refluxed in 40 ml of 6N hydrochloric acid for 3 hrs. After cooling, the reaction mixture was concentrated under reduced pressure so as to reduce the volume of the solution to about 1/10. Then, 46 ml of isopropyl alcohol was added at room temperature and the resulting mixture was stirred for 4 hours. The precipitate thus formed was taken up by filtration and dried under reduced pressure to thereby give 4.7 g of the title compound (yield: 93.6%). m.p.: 173°–176° C.

IR spectrum (KBr) $v_{max}$: 2950 $cm^{-1}$, 1700 $cm^{-1}$.

NMR spectrum (DMSO, internal standard: tetramethylsilane, δ ppm):

1.6–1.8 (4H, m); 2.7–2.9 (2H, m); 3.1–3.3 (2H, m); 7.9–8.0 (1H, m); 8.0–8.3 (2H, b); 8.7–9.4 (3H, m); 9.4–10.4 (2H, b).

Example 3: Synthesis of 2-(3-pyridyl)-3,4,5,6-tetrahydropyridine (compound of the formula (IV): anabaseine)

9.9 g (mixture of keto-enol tautomers, 43 mmol) of the 3-nicotinoyl-1-vinyl-2-piperidinone obtained in Example 1 was dissolved in 12 ml of tetrahydrofuran and added to 55 ml of 6N hydrochloric acid under reflux at 80° to 100° C. After stirring at 85° C. for 3 hours, the reaction mixture was cooled to 10° C. or below. Then, the pH value of the mixture was adjusted to about 11 by adding a 10M aqueous solution of sodium hydroxide at 10° to 30° C. The resulting aqueous solution was extracted with 40 ml portions of dichloromethane thrice and dried with sodium sulfate. After evaporating the dichloromethane under reduced pressure, 6.5 g of the title compound was obtained as an oily residue (yield: 94.5%). NMR spectrum (CDCl$_3$, internal standard: tetramethylsilane, δ ppm):

1.5–2.0 (4H, m); 2.5–2.7 (2H, m); 3.8–3.9 (2H, m); 7.2–9.0 (4H, m).

Reference Example: Synthesis of 3-(5-amino-1-pentanoyl)-pyridine dihydrochloride (dihydrochloride of compound of the formula (III))

6.5 g (41 mmol) of the 2-(3-pyridyl)-3,4,5,6-tetrahydropyridine obtained in Example 3 was dissolved in 123 ml of isopropanol. At a temperature of 30° C. or below, 6.9 ml of conc. hydrochloric acid was added thereto and the mixture was stirred at room temperature for 3 hours. Then, the reaction mixture was cooled at 5° C. or below for 2 hours. The precipitate thus formed was taken up by filtration, washed with isopropyl alcohol and dried under reduced pressure to thereby give 7.7 g of the title compound (yield: 74.6%).

Comparative Example 1: Synthesis of compound (IV)

In order to compare with the present invention, the compound (IV) was synthesized in accordance with the method described in Chem. Ber., 69, 1082–1085 (1936). Namely, 4.06 g (20 mmol) of N-benzoyl-2-piperidone, 3.03 g (20 mmol) of ethyl nicotinate and 8 ml of benzene were introduced into a flask. Further, 1.84 g (27 mmol) of sodium ethoxide was added thereto and the resulting mixture was heated under reflux for 5 hours. Then, the reaction mixture was evaporated to dryness. To the obtained residue was added 59 ml of conc. hydrochloric acid and the mixture was heated under reflux at 110° C. for 2 hours. The reaction mixture was cooled and a 10M aqueous solution of sodium hydroxide was added thereto at 14° to 30° C. until the pH value reached 10.3. Then, it was extracted with 60 ml portions of dichloromethane twice. The organic layers were combined, washed with a saturated aqueous solution of sodium chloride and then dried with Na$_2$SO$_4$. After filtering off the Na$_2$SO$_4$, the filtrate was concentrated and the residue was purified by silica gel chromatography (developing solvent: chloroform, ethanol) to thereby give 1.87 g of the title compound (yield: 58.4%).

Comparative Example 2:

The procedure of Comparative Example 1 was repeated except for replacing the benzene employed as the solvent by tetrahydrofuran (THF). Thus, 1.35 g of the compound (IV) was obtained (yield: 42.2%).

Comparative Example 3:

The procedure of Comparative Example 1 was repeated except for replacing the N-benzoyl-2-piperidone employed as the starting material by N-trimethylsilyl(TMS)-2-piperidone. Thus, 0.38 g of the compound (IV) obtained (yield: 23.8%).

Comparative Example 4:

The procedures of Examples and Reference Example were followed except for replacing the sodium alkoxide employed as the base by sodium hydride. Thus, 9.14 g of dihydrochloride of the compound (III) was obtained (yield: 71.8%).

Comparative Example 5:

Under a nitrogen gas stream, 6.25 g (50 mmol) of N-vinylpiperidone and 27 ml of tetrahydrofuran were introduced into a flask and cooled to −60° C. Then, 32 ml of a solution of n-butyllithium in hexane (1.6 mol/l) was added dropwise thereto at −50° to −60° C. and the resulting mixture was stirred at the same temperature for 20 minutes. To the solution thus obtained was added dropwise 7.55 g (50 mmol) of ethyl nicotinate at −50° to −60° C. and the resulting mixture was stirred at the same temperature for 20 minutes. Then, the reaction mixture was heated and stirred at room temperature for 5 hours. After the completion of the reaction, 60 ml of a saturated aqueous solution of ammonium chloride was added and the mixture was quenched. After extracting with 70 ml portions of ethyl acetate thrice, the extracts were dried with anhydrous sodium sulfate. Then, the sodium sulfate was filtered off and the filtrate was concentrated under reduced pressure to thereby give 6.8 g of a residue. This residue was subjected to successive treatments by the same methods as described in Example 3 and Reference Example. Thus, 0.68 g of dihydrochloride of the compound (III) was obtained (yield: 5.4%).

Comparative Example 6:

Under a nitrogen gas stream, 3.5 ml (50 mmol) of diisopropylamine and 12 ml of tetrahydrofuran were introduced into a flask and cooled to −30° C. Then, 32 ml of a solution of n-butyllithium in hexane (1.6 mol/l) was added dropwise thereto at −20° to −30° C. and the resulting mixture was stirred at the same temperature for 20 minutes to thereby give a solution of lithium diisopropylamide (LDA). This solution was cooled to −60° C. and then a solution of 6.25 g (50 mmol) of N-vinylpiperidone in 15 ml of tetrahydrofuran was added dropwise thereto at −50° to −60° C. The resulting mixture was further stirred at this temperature for 20 minutes. The resulting solution was treated in the same manner as described in Comparative Example 5 with the use of 7.55 g (50 mmol) of ethyl nicotinate. Thus, 3.55 g of dihydrochloride of the compound (III) was obtained (yield: 28.3%).

Tables 1 and 2 show the results of the above Examples and Comparative Examples.

Table 1 shows a comparison of the yields of the compound (IV) depending on the N-protecting groups of 2-piperidone and solvents. The yield of Example means the yield of the compound (IV) obtained from the starting material of Example 1 through the reaction of Example 3.

Table 2 shows a comparison of the yields of dihydrochloride of the compound (III) depending on bases. The yield of Example means the yield of dihydrochloride of the compound (III) obtained from the starting material of Example 1 through the reaction of Example 3 followed by the treatment of Reference Example.

TABLE 1

| Example No. | N-Protecting Group of 2-Piperidone | Base | Solvent | Yield of Compound (IV) (%) |
| --- | --- | --- | --- | --- |
| Example | vinyl | NaOEt | THF | 81.3 |
| Comp. Example 1 | benzoyl | NaOEt | benzene | 54.2 |
| Comp. Example 2 | benzoyl | NaOEt | THF | 42.2 |
| Comp. Example 3 | TMS | NaOEt | benzene | 23.8 |

TABLE 2

| Example No. | N-Protecting Group of 2-Piperidone | Base | Solvent | Yield of Compound (III) (%) |
|---|---|---|---|---|
| Example | vinyl | NaOEt | THF | 64.6 |
| Comp. Example 4 | vinyl | NaH | THF | 71.8 |
| Comp. Example 5 | vinyl | n-BuLi | THF | 5.4 |
| Comp. Example 6 | vinyl | LDA | THF | 28.3 |

In the reaction according to the present invention, no rapid change in temperature was observed and scarcely any side-product was formed. In Comparative Example 4, vigorous foaming was observed in the reaction together with the heat generation and the evolution of hydrogen gas.

A comparison among the results of Examples and Comparative Examples 1 to 3 indicates that the yield can be elevated by using a vinyl group as the protecting group. Also, a comparison among the results of Examples and Comparative Examples 4 to 6 indicate that the yield achieved by using sodium ethoxide as a base is almost comparable to the yield achieved with the use of sodium hydride.

INDUSTRIAL APPLICABILITY

The compounds and production processes of the present invention are useful as production intermediates of pyridine derivatives represented by the following formulae (III) and (IV):

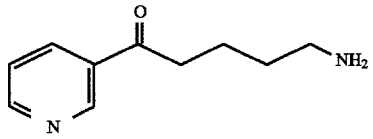
(III)

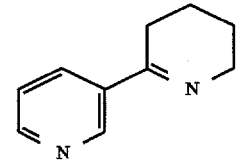
(IV)

which are useful as a remedy for central nervous system diseases such as Alzheimer's disease and Parkinson's disease, and methods for producing the same.

We claim:

1. A compound represented by formula (V):

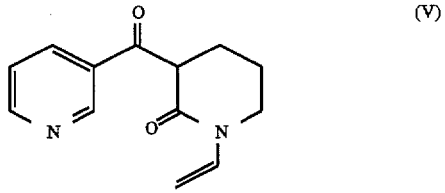
(V)

its tautomer and a mixture of the same.

2. A process for producing a compound represented by the formula (V), its tautomer or a mixture of the same as claimed in claim 1, which comprises reacting N-vinylpiperidone represented by formula (I):

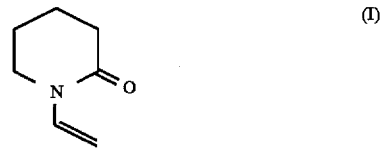
(I)

with a nicotinate represented by formula (II):

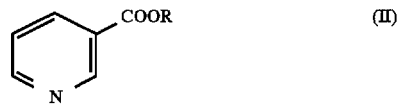
(II)

wherein R represents a lower alkyl group; in the presence of a sodium alkoxide.

3. The process for producing a compound represented by the formula (V), its tautomer or a mixture of the same as claimed in claim 2, wherein said sodium alkoxide is sodium ethoxide.

4. The process for producing a compound represented by the formula (V), its tautomer or a mixture of the same as claimed in claim 2, wherein R in the formula (II) is an ethyl group and said sodium alkoxide is sodium ethoxide.

* * * * *